United States Patent
Tin

(10) Patent No.: US 9,274,052 B2
(45) Date of Patent: Mar. 1, 2016

(54) FEATURE VECTOR FOR CLASSIFYING SPECULAR OBJECTS BASED ON MATERIAL TYPE

(71) Applicant: CANON KABUSHIKI KAISHA, Tokyo (JP)

(72) Inventor: Siu-Kei Tin, Milpitas, CA (US)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 14/287,814

(22) Filed: May 27, 2014

(65) Prior Publication Data

US 2015/0015887 A1   Jan. 15, 2015

Related U.S. Application Data

(60) Provisional application No. 61/910,218, filed on Nov. 29, 2013, provisional application No. 61/844,797, filed on Jul. 10, 2013.

(51) Int. Cl.
*G01N 21/00* (2006.01)
*G01N 21/55* (2014.01)
(Continued)

(52) U.S. Cl.
CPC .............. *G01N 21/55* (2013.01); *G01N 21/314* (2013.01); *G01N 33/20* (2013.01)

(58) Field of Classification Search
CPC .................... G01N 2015/149; G01N 15/1459; G01N 15/1484; G01N 2015/1481; G01N 15/1404; G01N 2015/1006; G01N 21/85; G01N 33/5005; G01N 15/1425; G01N 2015/1406; G01N 2021/845; G01N 21/27; G01N 21/6428
See application file for complete search history.

(56) References Cited

U.S. PATENT DOCUMENTS 3,747,755 A    7/1973   Senturia et al. ............ 209/111.5
6,496,594 B1 * 12/2002  Prokoski ....................... 382/118
(Continued)

FOREIGN PATENT DOCUMENTS

EP    0 968 772    1/2000
EP    2 187 339    5/2010
(Continued)

OTHER PUBLICATIONS

Artzai Picón, et al. "Fuzzy Spectral and Spatial Feature Integration for Classification of Nonferrous Materials in Hyperspectral Data", IEEE Transactions on Industrial Informatics, vol. 5, No. 4, Nov. 2009, pp. 483-494.

*Primary Examiner* — Michael P Stafira
(74) *Attorney, Agent, or Firm* — Fitzpatrick, Cella, Harper & Scinto

(57) ABSTRACT

Material classification for a sample fabricated from an unknown material, particularly a specular sample such as a metallic sample fabricated from an unknown metal. A measurement is obtained of a specular reflection of the sample at at least one observation angle and in at least two spectral bands including first and second spectral bands; a feature vector is calculated using a homogeneous function that combines the measured specular reflections in the first and second spectral bands; and the sample is classified based on the feature vector. The homogeneous function may include a ratio of values of the first and second spectral bands of the measured specular reflections, and the feature vector may be based on a histogram of such ratio values. Classification may include determining a distance between the feature vector of the sample and a feature vector of a reference sample in a predetermined database of labeled samples.

17 Claims, 9 Drawing Sheets

(51) Int. Cl.
*G01N 33/20* (2006.01)
*G01N 21/31* (2006.01)

(56) References Cited

U.S. PATENT DOCUMENTS

| | | | |
|---|---|---|---|
| 7,449,655 B2 | 11/2008 | Cowling et al. | 209/577 |
| 8,124,931 B2 * | 2/2012 | Andrews et al. | 250/301 |
| 2010/0080456 A1 * | 4/2010 | Paul et al. | 382/165 |
| 2010/0290032 A1 | 11/2010 | Bugge | 356/51 |

FOREIGN PATENT DOCUMENTS

| | | |
|---|---|---|
| GB | 2 119 509 | 4/1983 |
| WO | 2013/102858 | 11/2013 |

* cited by examiner

FEATURE VECTOR FOR CLASSIFYING SPECULAR OBJECTS BASED ON MATERIAL TYPE

CROSS-REFERENCE TO RELATED APPLICATION

This application claims benefit under 35 U.S.C. §119 of U.S. Provisional Application No. 61/910,218 filed Nov. 29, 2013, and of U.S. Provisional Application No. 61/844,797 filed Jul. 10, 2013, the entire contents of both of which are incorporated herein by reference as if set forth in full.

FIELD

The present disclosure relates to material classification in which an object fabricated from an unknown material is illuminated with light, and light reflected therefrom is measured in an effort to identify the unknown material.

BACKGROUND

Optical determination of the material type of a sample is appealing in many applications, such as recycling, because it requires no contact. For opaque materials, such as metals, the bidirectional reflectance distribution function (BRDF) describes the optical response (reflection) of the material to incident light from different directions. This response may be used to characterize or classify materials. Because the BRDF is a 4-dimensional function of illumination (solid) angle and observation (solid) angle, typically only "slices" of it are measured, and a classifier is computed from these slices.

Some materials present themselves quite similarly to the classifier, and are thus difficult to classify by conventional means. As an example, metals of similar color can be difficult to distinguish from each other. FIG. 1 shows an example, in which the metals titanium, nickel and aluminum appear quite similar to one another, and are thus difficult to classify. Situations such as this may be challenging to conventional Computer Vision algorithms using RGB images only.

SUMMARY

BRDF does not depend only on the material, but also on the surface condition. For example, for the same metal, for example aluminum, different surface finishing will result in completely different BRDF. A smooth, mirror-like metal surface has a BRDF that is concentrated along the specular directions, i.e., looks like a delta function. A metal surface that is rough may behave more like a Lambertian surface, i.e., the BRDF is constant for all illumination and all observation angles.

For materials exhibiting specular reflection, such as metal materials, specular reflection is a result of scattering of light by moving electrons on the metal surface. There is no subsurface phenomenon. It has been found that a metal surface can be adequately modeled by a microfacet model, which postulates a distribution of microscopic mirrors, or microfacets. Using this model, the diffuse reflection term arises from interreflections among the microfacets.

A prior application filed by the Applicant herein is U.S. Provisional Application No. 61/844,797, "Devices, Systems, And Methods for Classifying Metals Based on a Bidirectional Reflectance Distribution Function That Discounts Roughness", filed Jul. 10, 2013. Such application describes, among other features, the use of a feature vector for material classification based on an estimated ratio value of at least two spectral bands of a measured specular reflection. As an example, the feature value is calculated for each pixel in the region corresponding to specular reflection. They will in general form a cluster. The center of the cluster is determined, after optionally removing any outliers. This results in a central feature value, or if multiple features are used, a central feature vector. This feature vector can be compared with a database of feature vector values for known materials to identify the material type of the sample. The contents of Application No. 61/844,797 are incorporated herein by reference, as if set forth in full herein.

The disclosure herein is based at least partly on the observation that information on the specular reflection need not necessarily be reduced to a single feature value for the ratio, as was the case in some of the embodiments described in the aforementioned Application No. 61/844,797. Rather, as described herein, multiple ratio values are obtained, and the entirety of the distribution of the ratio values is exploited in order to improve accuracy of material classification, particularly in the case of materials like metals which exhibit specular reflection.

In addition, as described herein, measurements of specular reflection may be made at more than one observation angle relative to a given illumination angle. For example, measurements of specular reflection may be made at both of a "small incident angle" and "grazing incident angle". An example of small incident angle is an approximate angle of 20 degrees. An example of grazing incident angle is an approximate angle of 75 degrees.

Aspects described herein include material classification of a sample fabricated from an unknown material comprising obtaining a measurement of a specular reflection of the sample at at least one observation angle and in at least two spectral bands; calculating feature vector using the at least two spectral bands of the measured specular reflections; and classifying the sample based on the feature vector.

According to such aspects, the sample may be a specular sample fabricated from an unknown material, such as a metallic sample fabricated from an unknown metal, and the measurement in at least two spectral bands may include a first spectral band and a second spectral band, wherein the calculation of the feature vector uses a homogeneous function such as a ratio of values that combines the measured specular reflections in the first and second spectral bands. The feature vector may be based on a histogram of ratio values of the first and second spectral bands of the measured specular reflections, for example, wherein the histogram of ratio values is based on ratio values from a selected region of pixels of the captured image that corresponds to a specular highlight. The selected region may be defined by a mask derived from the captured image of the specular reflection.

Further according to such aspects, and so as to generate the specular reflection from the sample, the sample may be positioned relative to an illumination source and the observation angle.

Classification according to this aspect may include a determination of a distance between the histogram of the sample and a histogram of a reference sample in a predetermined database. Multiple histograms may be associated with a reference sample in the predetermined database, and a distance between the sample and the reference sample may in this case be taken to be a minimum of distances of the histogram of the sample from the multiple histograms of the reference sample.

The obtained measurements may be taken at a respective multiplicity of observation angles including a grazing incident angle and a small incident angle. In particular, for a multiplicity of observation angles, a histogram of ratio values of the first and second spectral bands of the measured specular reflections may be obtained for each observation angle, resulting in multiple histograms of ratio values each respectively corresponding to one of the multiple observation angles, such that classification may be based on a distance between the multiple histograms of the sample and the multiple histograms of a reference sample in the predetermined database. The histograms may be weighted by weighting factors that depend on specific materials being differentiated.

According to further aspects, classification may include a determination of a distance between the feature vector of the sample and a feature vector of a reference sample in a predetermined database of labeled samples. Multiple feature vectors may be associated with a reference sample in the predetermined database, such that a distance between the sample and the reference sample may be taken to be a minimum of distances of the feature vector of the sample from the multiple feature vectors of the reference sample. As in other aspects, multiple measurements may be taken at a respective multiplicity of observation angles including a grazing incident angle and a small incident angle. In particular, for a multiplicity of observation angles, a feature vector may be obtained for each observation angle, resulting in multiple feature vectors each respectively corresponding to one of the multiple observation angles, such that classification may be based on a distance between the multiple feature vectors of the sample and the multiple feature vectors of a reference sample in the predetermined database. The feature vectors may be weighted by weighting factors that depend on specific materials being differentiated.

According to further aspects, the obtained measurements may include captures of an image of specular reflection in at least two spectral bands. A histogram of ratio values may be based on ratio values from a selected region of pixels of the captured image that corresponds to a specular highlight. Such regions may be defined by a mask derived from a captured image of the specular reflection.

Further according to such aspects, classifying includes determining a distance between the histogram of the sample and a histogram of a reference sample in a predetermined database. Multiple histograms may be associated with a reference sample in the predetermined database, and a distance between the sample and the reference sample is taken to be a minimum of distances of the histogram of the sample from the multiple histograms of the reference sample.

Further according to such aspects, multiple measurements may be taken at a respective multiplicity of observation angles such as a grazing incident angle and a small incident angle. The measurements may be combined in a weighting arrangement that depends on specific materials being differentiated, so as to improve classification accuracy.

An advantageous effect is thereby obtained, wherein hard-to-separate materials such as metals may be classified in as few as one shot (with commodity equipment such as an RGB projector and an RGB camera) when specular reflection can be obtained.

This brief summary has been provided so that the nature of this disclosure may be understood quickly. A more complete understanding can be obtained by reference to the following detailed description and to the attached drawings.

DETAILED DESCRIPTION

Figure 2:
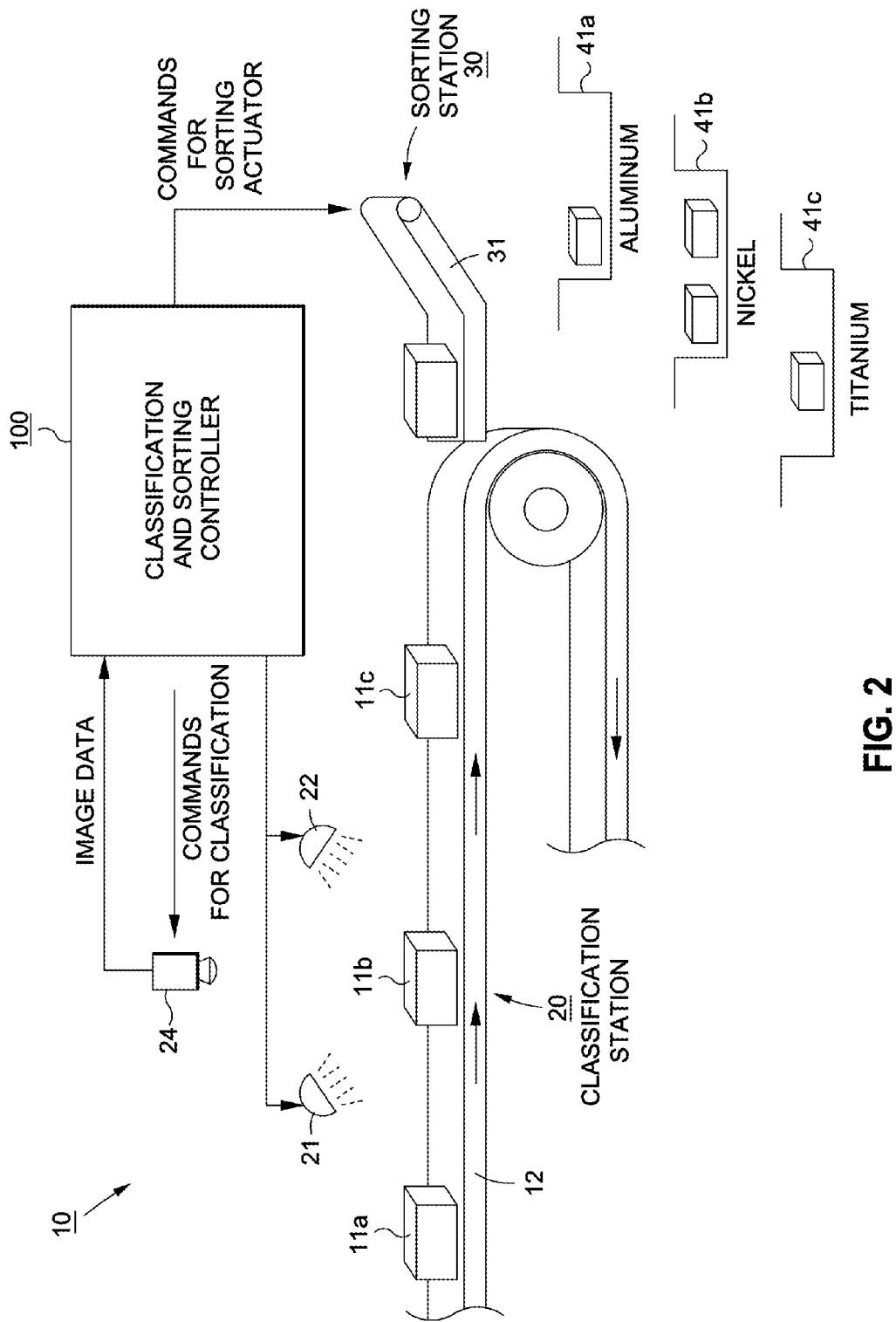
FIG. 2 is an example embodiment of a classification system according to the description herein, in the form of a recycling system in which objects to be recycled are classified according to the materials from which the objects are fabricated, and the classified objects are sorted for recycling according to their material classification.

FIG. 2 is an example embodiment of a classification system according to the description herein, in the form of a recycling system 10 in which objects to be recycled are classified according to the materials from which the objects are fabricated, and the classified objects are sorted for recycling according to their material classification. As shown in FIG. 2, objects 11a, 11b, etc. are conveyed on a conveyor mechanism 12 to a classification station 20, where the objects are classified according to their material, and thence to a sorting station 30, where the objects are sorted according to their material classification. Classification station 20 includes plural light sources 21 and 22, together with a camera 24 for capturing images of objects positioned at classification station 20. The object at the classification station is illuminated individually by each of the plural light sources under control of classification and sorting controller 100, and camera 24 captures one or more images for each individual illumination. Under control of the classification and sorting controller 100, a classification is made for the material from which the object is fabricated.

Conveyor mechanism 12 continues to convey the object to sorting station 30, where sorting actuator 31 sorts the objects according to the material classification. Sorting is controlled by classification and sorting controller 100, which commands actuator mechanism 31 to sort the classified objects into multiple receptacles 41a, 41b and 41b.

In this example embodiment, material classification differentiates between different types of metals from which the objects are fabricated, such as aluminum, nickel and titanium. These metallic samples are examples of a broader class of specular samples which exhibit specular reflection and are fabricated from an unknown material. Naturally, it will be understood that this is a non-limiting example. In addition, other embodiments might include a classification of "unknown", signifying that material classification did not succeed with confidence, with a corresponding receptacle for which manual sorting or other further processing is required.

Figure 3:
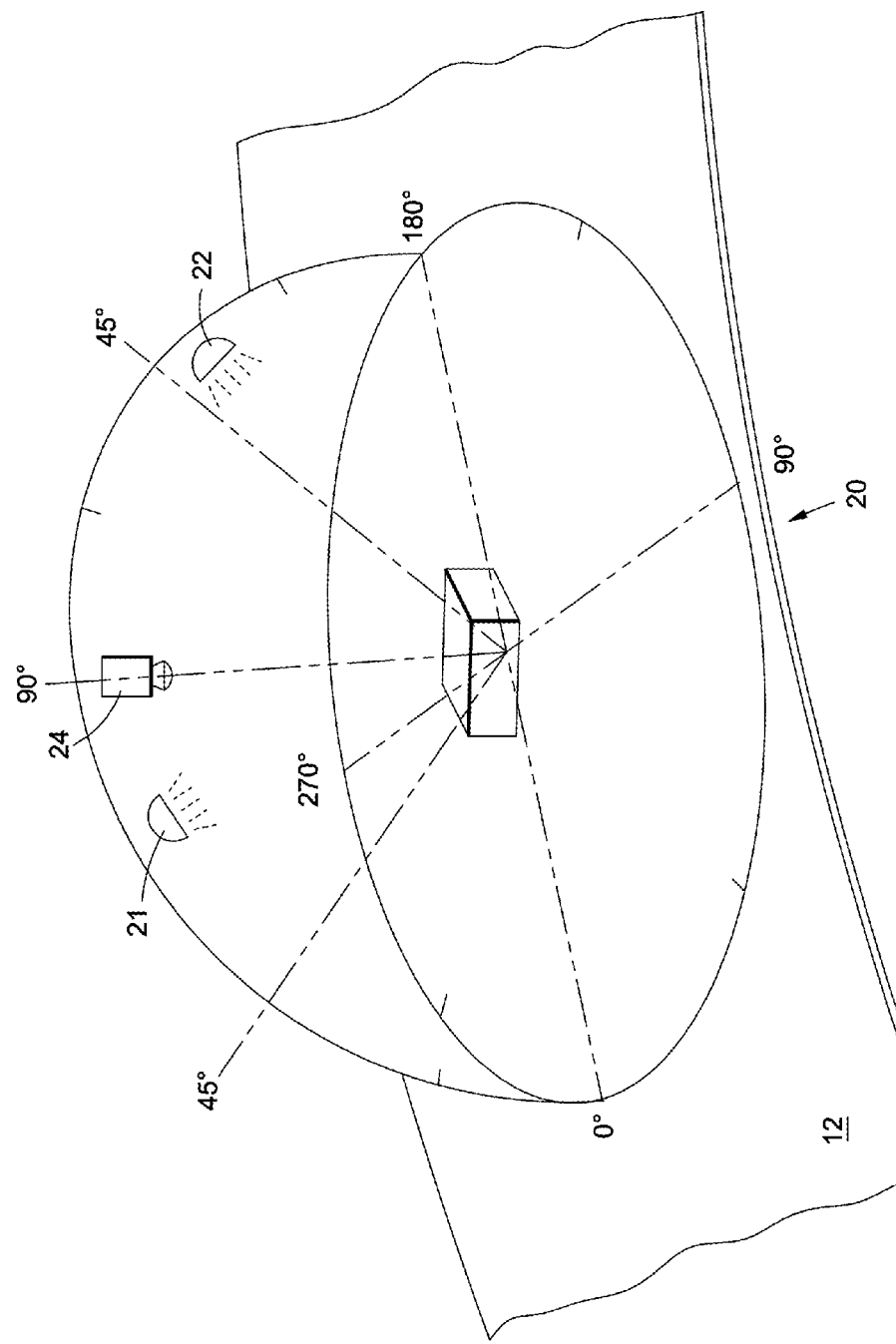
FIG. 3 is a more detailed view of an object being subjected to classification at a classification station of the FIG. 2 view.

FIG. 3 is a more detailed view of an object on conveyor mechanism 12 at classification station 20. In this figure, light sources 21 and 22, which are multispectral light sources as described below, are positioned at illumination angles to illuminate an object at the classification station 21, and camera 24, which is a multispectral camera as described below, is positioned at an observation angle. Light sources 21 and 22 are positioned so as to obtain specular reflection at both of a small incidence angle and a grazing incidence angle, as also described below.

Under control of classification and sorting controller 100, each light source 21 and 22 is illuminated. For each such illumination, camera 24 captures an image of specular light reflected from the object. The captured images are collected by classification and sorting controller 100, and are analyzed thereby, as described below, so as to obtain a classification of the material from which the illuminated object is fabricated.

Figure 4:
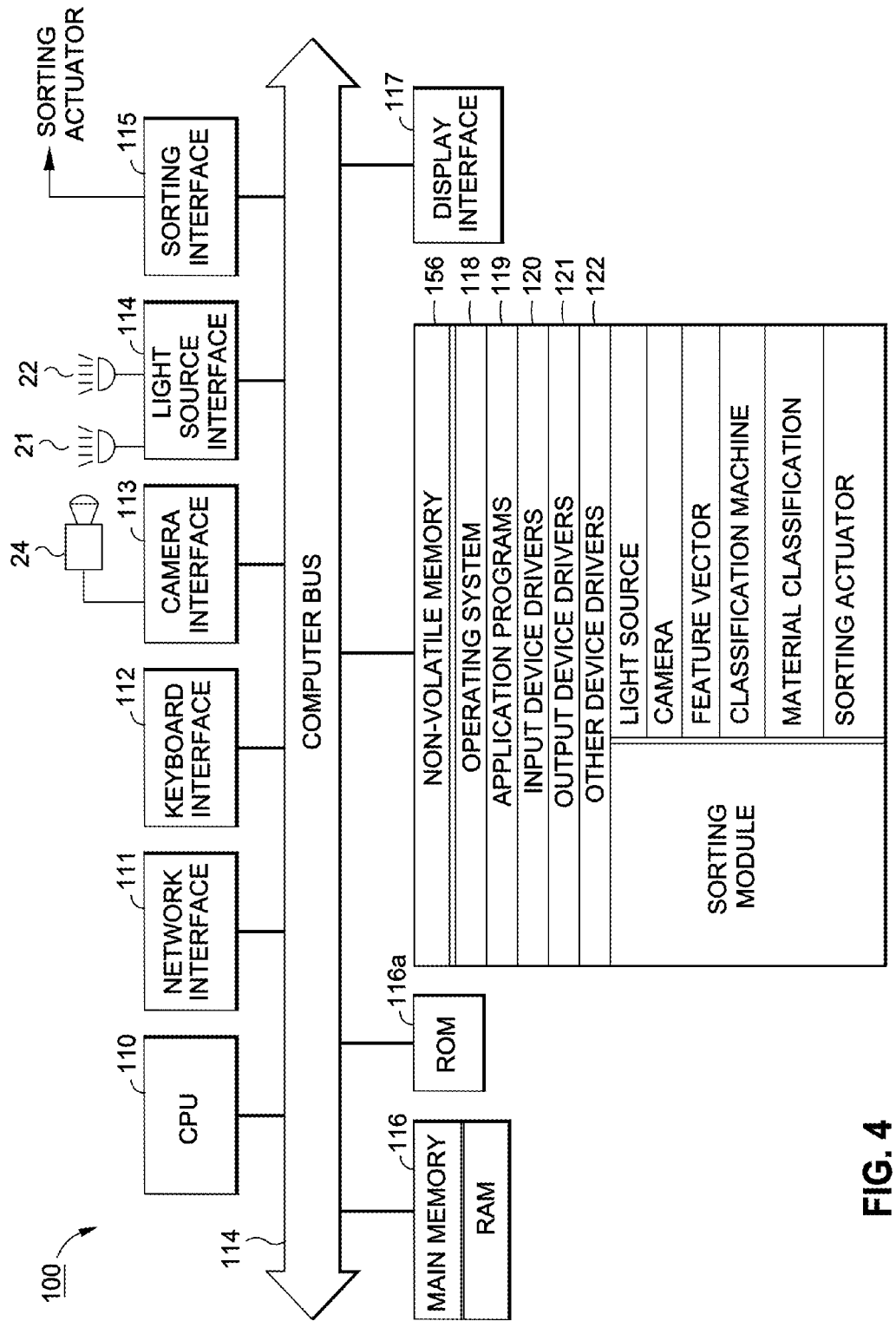
FIG. 4 is a view for explaining the architecture of a classification and sorting controller.

FIG. 4 is a view for explaining the architecture of classification and sorting controller 100.

As shown in FIG. 4, classification and sorting controller 100 includes central processing unit (CPU) 110 which interfaces with computer bus 114. This embodiment uses a single CPU but it will be understood that other embodiments may be configured differently, such as with multiple CPUs, with one or more multi-core CPUs, or with a distributed network of CPUs. Also interfacing with computer bus 114 are non-volatile memory 156 (e.g., a hard disk or other nonvolatile storage medium), network interface 111, keyboard interface 112, camera interface 113, random access memory (RAM) 116 for use as a main run-time transient memory, read only memory (ROM) 116a, and display interface 117 for a display screen or other output.

RAM 116 interfaces with computer bus 114 so as to provide information stored in RAM 116 to CPU 110 during execution of the instructions in software programs, such as an operating system, application programs, image processing modules, and device drivers. More specifically, CPU 110 first loads computer-executable process steps from non-volatile memory 156, or another storage device into a region of RAM 116. CPU 110 can then execute the stored process steps from RAM 116 in order to execute the loaded computer-executable process steps. Data, also, can be stored in RAM 116 so that the data can be accessed by CPU 110 during the execution of the computer-executable software programs, to the extent that such software programs have a need to access and/or modify the data.

As also shown in FIG. 4, non-volatile memory 156 contains computer-executable process steps for operating system 118, and application programs 119, such as graphic image management programs. Non-volatile memory 156 also contains computer-executable process steps for device drivers for software interface to devices, such as input device drivers 120, output device drivers 121, and other device drivers 122.

Non-volatile memory 156 also stores a sorting module, which may comprise computer-executable process steps for material classification of an object fabricated from an unknown material, and for sorting the object based on the material classification.

The computer-executable process steps for these modules may be configured as part of operating system 118, as part of an output device driver in output device drivers 121, or as a stand-alone application program. These modules may also be configured as a plug-in or dynamic link library (DLL) to the operating system, device driver or application program. It can be appreciated that the present disclosure is not limited to these embodiments and that the disclosed modules may be used in other environments.

Non-volatile memory 156, RAM 116, and ROM 116a are examples of non-transitory computer-readable memory media on which are stored computer-executable process steps for execution by a computer processor. It can be appreciated that the present disclosure is not limited to these examples of non-transitory memory.

The sorting module includes a corresponding plurality of modules for control of the light sources, for control of the camera(s) and for gathering of image data of such camera(s) a module for derivation of feature values such as histograms representing the distribution of ratios of certain ones of spectral wavelengths recorded by the camera, and a classification machine. The classification machine accepts as inputs the feature vectors derived by the feature vector module, and provides a classification of the material from which the object under inspection is fabricated, such as by comparison of the histogram distribution to a reference database.

In addition, there are modules related to use of the material classification from the classification machine, and actuation of the sorting mechanism based on the classification.

Figure 5:
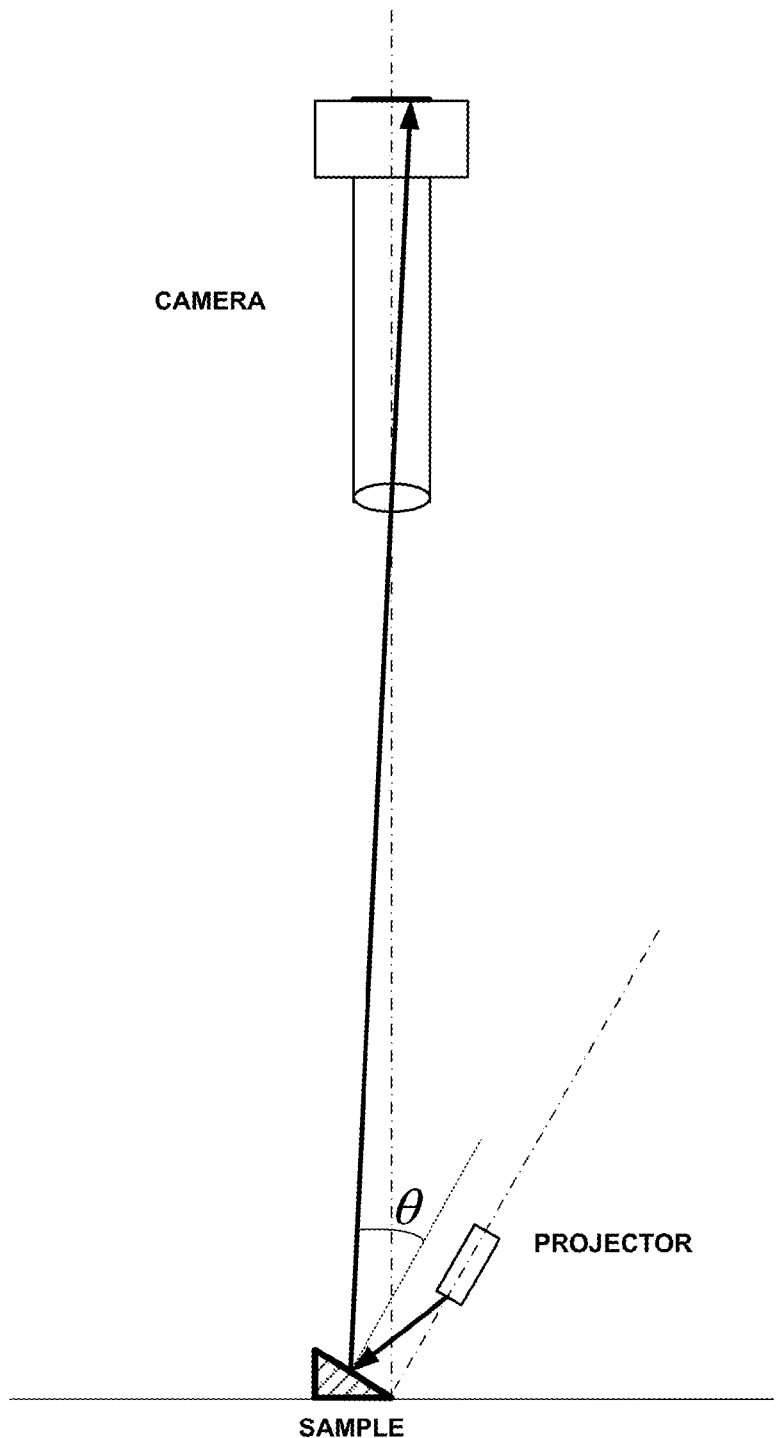
FIG. 5 is a view for explaining the orientation and configuration of the camera relative to a projection light source.

FIG. 5 is a view for explaining the orientation and configuration of camera 24 relative to one or the other of light sources 21 and 22. In this figure and elsewhere in the application, the light sources are sometimes referred to as "projectors".

For the projectors, each has at least two channels, each corresponding to a spectral band. In one embodiment, the two channels have wavelengths (red) and (blue). An RGB laser projector, for example, satisfies this requirement.

For the camera, it has sensitivity commensurate with the channels of the projector, and is thus capable of detecting the spectral bands of the projector.

A monochrome (panchromatic) camera can satisfy this requirement if the projector projects the wavelengths separately and the camera captures the respective image.

A color/multispectral camera (e.g., an RGB camera) can satisfy this requirement if the wavelengths of the projector can be separated by the different channels of the camera, possibly with post-processing to unmix if each channel of the camera is sensitive to more than one wavelength of the projector. In this case, it is possible that the projector projects all wavelengths simultaneously and the camera captures a single image, i.e., in one shot.

In FIG. 5, $\theta$ is the angle at which specular reflection occurs. This description distinguishes between the case of a "small incident angle" and a "grazing incident angle". An example of small incident angle is an approximate angle of 20 degrees. An example of grazing incident angle is an approximate angle of 75 degrees.

Figure 6:
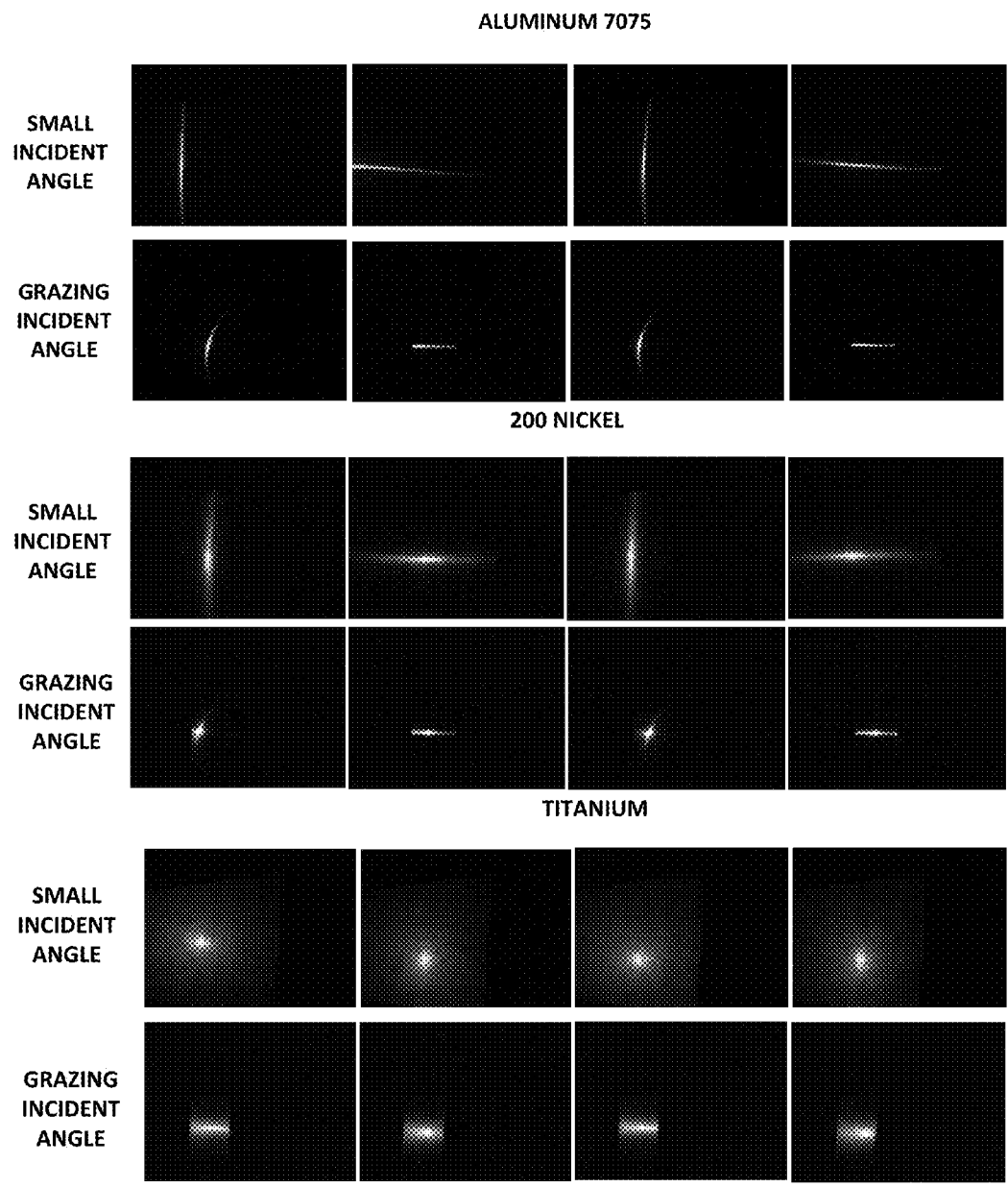
FIG. 6 shows example images of specular reflection of the three (3) metals, aluminum, nickel and titanium, as captured at a small incident angle and at a grazing incident angle.

FIG. 6 shows example images of specular reflection of the three (3) metals, aluminum 7075, 200 nickel and titanium, as captured at a "small incident angle" and at a "grazing incident angle" using the camera/projector configuration described above.

The images for different metals look different visually and show promise as a basis for a feature vector for classification. In particular, the aluminum and nickel samples are clearly anisotropic (possibly due to surface mesostructure), whereas the titanium sample is to a large degree isotropic. Practical use of these images may be enhanced by processing them in such a way as to consistently extract a numerical feature that can be used for comparison purpose. Two techniques are described herein, the first being normalization and the second being determination of a mask by which useful areas of the specular reflection are extracted for processing into histograms of ratios of red-to-blue wavelengths.

Concerning the first technique of normalization of the images, normalization is often helpful in consistently determining a usable region of the image that corresponds to substantial specular reflection (i.e., the aforementioned mask). A simple fixed threshold for the pixel value is not expected to work well because different metals have different spectral reflectance. In addition, it is beneficial to discard pixels that are saturated (due to sensor saturation, which is very common near specular highlights) and also to ignore also pixels that are too close to the noise floor.

Figure 7:
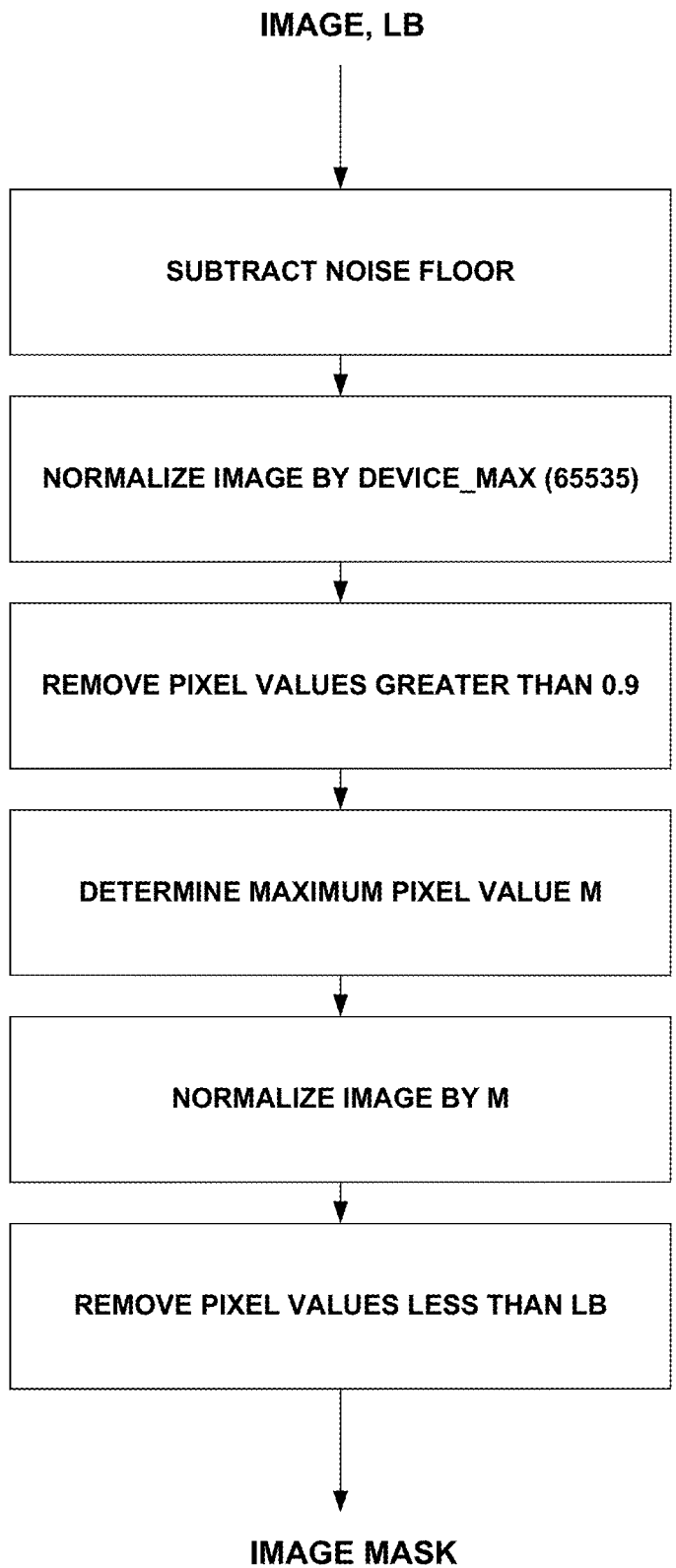
FIG. 7 is a flow diagram showing both normalization processing and mask determination for specular images.

FIG. 7 is a flow diagram showing both normalization processing and mask determination for the specular images. In this figure, it is assumed that the wavelengths are (red) and (blue), and that the ratio values being calculated are red-to-blue ratio values of "red"/"blue". The usable region of each image will be determined by the blue image and the FIG. 7 flow diagram, and the FIG. 7 flow diagram also determines an image mask that selects the usable region.

The inputs to the algorithm are an image, which is the "blue image" as mentioned earlier, and a lower bound threshold LB. In one example, LB=0.1.

A dark image is pre-captured (e.g., with the lens cap on) to account for the thermal noise. This image is subtracted from the input image as a preprocessing step. Digital images are encoded with a nominal range. For example, 16-bit images have a nominal maximum value DEVICE_MAX of 65535. The image is normalized relative to DEVICE_MAX for convenience. This step is convenient but not absolutely necessary.

Saturated pixels are then removed by removing pixels with value greater than 0.9. A pixel value of 1.0 (after the DEVICE_MAX normalization) is certainly saturated, but a value close to 1.0 can also be the average of some saturated readings during the exposure. This embodiment uses a conservative threshold of 0.9.

Next there is a determination of the maximum value M from the remaining pixels. This should be the camera reading at specular reflection.

Next the remaining pixels are normalized by dividing by the specular value M.

Usable pixels are selected whose pixel values are in the range from LB to 1.0. This corresponds to a range before normalization by M: LB*M to M.

Figure 8:
FIG. 8 shows an example image mask calculated from the flow diagram shown in FIG. 7.

FIG. 8 shows an example image mask calculated from the flow diagram shown in FIG. 7. The mask is a binary mask in which a value of 0 indicates that the corresponding pixel in the specular image is not used, and value of 1 indicates that the corresponding pixel in the specular image is used for calculation of a histogram of ratios of red-to-blue.

For each pixel selected by the mask, the ratio is calculated of red pixel value to blue pixel value, where both have already been corrected by subtracting the noise floor.

The ratios can be used in either of two different modes: a calibrated mode and an uncalibrated mode, wherein calibration refers primarily to compensation for projector radiance and/or camera sensitivities The ratios are used directly in the "uncalibrated mode". In particular, in the uncalibrated mode, there is typically no need to make off-line measurements of projector radiance and/or camera sensitivities. The uncalibrated mode may be adequate if the system parameters are fixed during run-time. The system parameters in question include projector settings that controls the laser intensity (for example) and camera settings such as aperture and exposure time. Even if the system parameters are fixed, system performance might still change over time due to usage and aging. In addition, the ratio will not relate to physical property (such as ratio of Fresnel factors) of the sample.

In the "calibrated mode", a correction factor is applied to the calculated ratio. For concreteness, denote the calculated ratio by and assume the red and blue images are taken with the same exposure time during run time (which is the case if a color camera/color filter array is used). In this embodiment, a correction factor k is determined such that $$k \cdot \frac{R}{B} = \frac{F_{\lambda_1}(\theta)}{F_{\lambda_2}(\theta)} \quad (1)$$

where $F_\lambda(\theta)$ denotes the Fresnel factor at wavelength $\lambda$ and incident angle $\theta$.

The following description gives an example procedure and prescription for determining k. The projector is controlled to project red and blue wavelengths successively onto a reference target and images taken by the camera. The reference target is preferably an approximate perfect diffuse reflector. A halon disk is an example. The exposure times for calibration are typically different from the run-time exposure because unlike specular reflection, diffuse reflection is much weaker and requires much longer exposure time.

An example calculation is illustrative. The red image of the halon disk is taken with an exposure time of 5000 msec. A small region near the center of the halon disk is cropped and average pixel value in this region is determined to be 439.24 (out of 16-bit range, and after removing the noise floor). The blue image of the halon disk is taken with an exposure time of 10000 msec and the average pixel value of the cropped region is determined to be 1155.87. The reflectances of the halon disk at 450 nm and 640 nm are measured by a spectrophotometer to be 0.9850 and 0.9732. The correction factor in this example is thus determined as:

$$k = \frac{0.9732}{0.9850} \cdot \frac{1155.87}{439.24} \cdot \frac{5000}{10000} = 1.3000 \quad (2)$$

The calibrated mode is desirable if the system may be used with different settings/parameters and/or system characteristics may shift over time. The reference data in the predetermined database will also be associated with known calibration status so that they will remain usable when different system settings are used at run-time.

Figure 9:
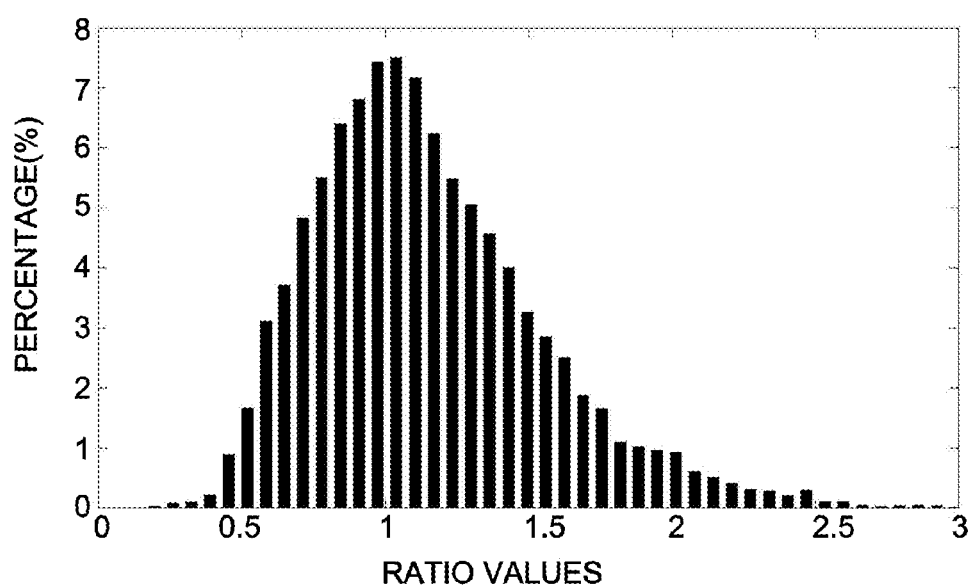
FIG. 9 shows an example histogram.

Either in the uncalibrated mode or the calibrated mode, a histogram is determined of ratio values for the pixels selected by the mask. FIG. 9 shows an example histogram.

The resulting histogram is typically unimodal, with the maximum frequency corresponding to the feature value proposed in the aforementioned Application No. 61/844,797.

In contrast, in the embodiments described herein, this histogram is used directly as a feature, such as by comparing the histogram to a database of reference histograms and selecting, as the classification, the material for the reference histogram having a smallest distance from the histogram determined for the unknown material. Furthermore, due to possible anisotropy of the material surface, for the reference histograms (stored in a predetermined database), there may be capture of multiple incident angles/multiple views of the same sample. In one embodiment, four (4) histograms are stored per sample per incident angle class (small incident angle or grazing incident angle).

Figure 10:
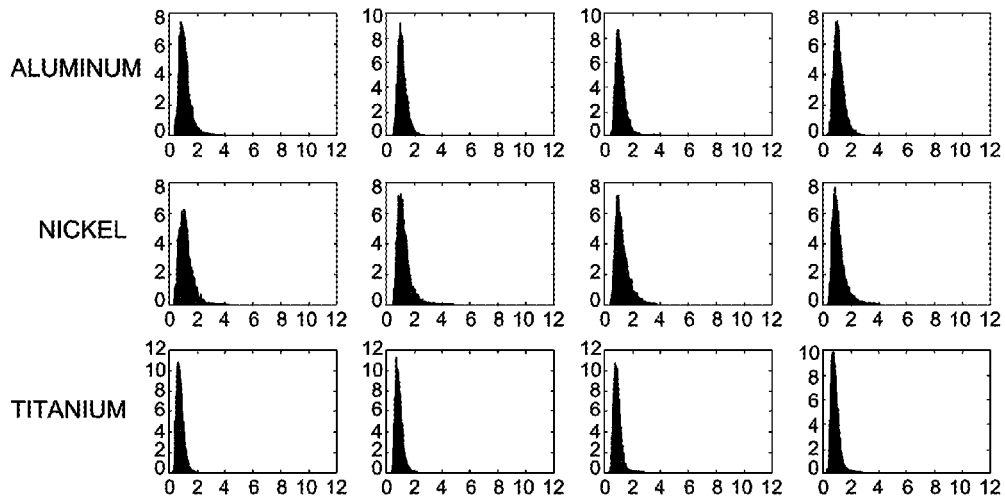
FIG. 10 shows four (4) reference histograms for aluminum, nickel and titanium for each of a small incident angle and a grazing incident angle.
Figure 10:
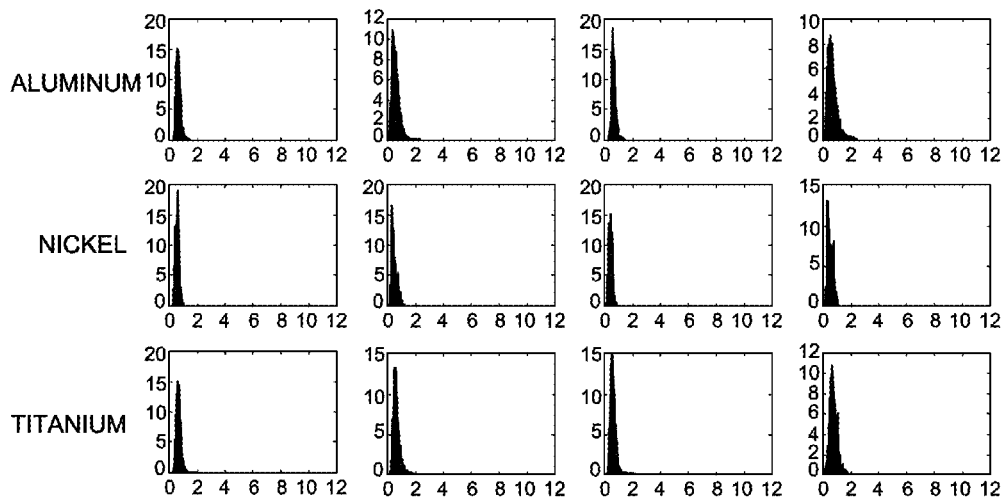

FIG. 10 shows the four (4) reference histograms for aluminum, nickel and titanium for each of the two incident angle classes (small incident angle or grazing incident angle).

During run-time with a test sample, the system captures a specular image or images that give rise to at least two images corresponding to two spectral bands. Together with capture of the spectral image, there is also capture of information signifying whether the incident angle is small or grazing. With the projector and camera geometrically calibrated, this can be determined if the 3D position and surface normal at the specular reflection are known. The aforementioned Application No. 61/844,797 may be referenced for embodiments to achieve this.

Each test sample x gives rise to a histogram, say h. A "distance" (designated herein by "d(x,X)") of this sample from a reference sample X stored in the database can be determined as follows. Assume that a reference sample is stored as a collection of N histograms. Furthermore, all histograms have the same bins where the number of bins is K.

$$d(x,X) = \min \chi(h, H_n) \quad (3)$$

where $\chi$ is a distance function for histograms and the minimum (min) in the above equation is taken over n=1, 2, ..., N. This embodiment uses the $\chi^2$ distance, defined for two histograms h and H with the same bins as:

$$\chi(h, H) = \sum_{k=1}^{K} \frac{(h(k) - H(k))^2}{h(k) + H(k)} \quad (4)$$

Other distance for histograms may be used, such as the Earth Mover's Distance (EMD).

The following Tables A and B show distances of test samples Al1, ..., Al16, Ni1, ..., Ni15, Ti1, ..., Ti16 (a total of 47 test cases) against reference Al, reference Ni and reference Ti. The two incident angle classes are shown separately. Boldface numbers represent the minimum among the 3 reference samples.

Table A, for the small incident angle case:

|        | Al1      | Al2      | Al3      | Al4      | Al5      | Al6      | Al7      | Al8      |
|--------|----------|----------|----------|----------|----------|----------|----------|----------|
| Al Ref | 0.020176 | 0.038285 | 0.019887 | 0.056839 | 0.025611 | 0.017847 | 0.027524 | 0.013347 |
| Ni Ref | 0.022777 | 0.015553 | 0.032231 | 0.023317 | 0.026368 | 0.018934 | 0.009901 | 0.028712 |
| Ti Ref | 0.228853 | 0.192523 | 0.205816 | 0.205987 | 0.234605 | 0.400771 | 0.409882 | 0.400637 |

|        | Al9      | Al10     | Al11     | Al12     | Al13     | Al14     | Al15     | Al16     |
|--------|----------|----------|----------|----------|----------|----------|----------|----------|
| Al Ref | 0.071401 | 0.040604 | 0.178609 | 0.130642 | 0.029626 | 0.071398 | 0.064901 | 0.177971 |
| Ni Ref | 0.042665 | 0.063183 | 0.12086  | 0.085029 | 0.021064 | 0.039109 | 0.053476 | 0.125813 |
| Ti Ref | 0.121384 | 0.114688 | 0.062845 | 0.084176 | 0.204706 | 0.173532 | 0.102067 | 0.152632 |

|        | Ni1      | Ni2      | Ni3      | Ni4      | Ni5      | Ni6      | Ni7      | Ni8      |
|--------|----------|----------|----------|----------|----------|----------|----------|----------|
| Al Ref | 0.040285 | 0.068504 | 0.055385 | 0.085524 | 0.161929 | 0.1742   | 0.174201 | 0.145758 |
| Ni Ref | 0.029935 | 0.025267 | 0.017762 | 0.039331 | 0.092208 | 0.104915 | 0.115767 | 0.076007 |
| Ti Ref | 0.172027 | 0.166167 | 0.211902 | 0.523835 | 0.076159 | 0.143112 | 0.098689 | 0.149313 |

|        | Ni9      | Ni10     | Ni11     | Ni12     | Ni13     | Ni14     | Ni15     |
|--------|----------|----------|----------|----------|----------|----------|----------|
| Al Ref | 0.065448 | 0.072406 | 0.10855  | 0.117317 | 0.230182 | 0.240487 | 0.167395 |
| Ni Ref | 0.029289 | 0.027551 | 0.051973 | 0.06008 | 0.137099 | 0.154075 | 0.0896 |
| Ti Ref | 0.185028 | 0.169868 | 0.217931 | 0.122055 | 0.650399 | 0.718967 | 0.628679 |

|        | Ti1      | Ti2      | Ti3      | Ti4      | Ti5      | Ti6      | Ti7      | Ti8      |
|--------|----------|----------|----------|----------|----------|----------|----------|----------|
| Al Ref | 0.193234 | 0.294955 | 0.207041 | 0.116031 | 0.267574 | 0.647039 | 0.326837 | 0.407319 |
| Ni Ref | 0.165056 | 0.24817  | 0.185574 | 0.102008 | 0.232676 | 0.568527 | 0.29575  | 0.360281 |
| Ti Ref | 0.013956 | 0.025476 | 0.015334 | 0.051238 | 0.007841 | 0.133844 | 0.013481 | 0.028242 |

|        | Ti9      | Ti10     | Ti11     | Ti12     | Ti13     | Ti14     | Ti15     | Ti16     |
|--------|----------|----------|----------|----------|----------|----------|----------|----------|
| Al Ref | 0.322111 | 0.162053 | 0.305995 | 0.186044 | 0.247273 | 0.089443 | 0.10126  | 0.108027 |
| Ni Ref | 0.283581 | 0.14232  | 0.271028 | 0.167878 | 0.214437 | 0.072689 | 0.095001 | 0.089065 |
| Ti Ref | 0.039589 | 0.024011 | 0.013242 | 0.015342 | 0.021136 | 0.082901 | 0.055934 | 0.057224 |

Table B, for the grazing incident angle case:

|        | Al1      | Al2      | Al3      | Al4      | Al5      | Al6      | Al7      | Al8      |
|--------|----------|----------|----------|----------|----------|----------|----------|----------|
| Al Ref | 0.071042 | 0.018396 | 0.02891  | 0.092048 | 0.04281  | 0.110142 | 0.03243  | 0.067834 |
| Ni Ref | 0.445978 | 0.155674 | 0.195021 | 0.155752 | 0.121879 | 0.16821  | 0.20041  | 0.120012 |
| Ti Ref | 0.094474 | 0.120332 | 0.020212 | 0.330512 | 0.221465 | 0.279106 | 0.202119 | 0.120531 |

|        | Al9      | Al10     | Al11     | Al12     | Al13     | Al14     | Al15     | Al16     |
|--------|----------|----------|----------|----------|----------|----------|----------|----------|
| Al Ref | 0.061566 | 0.195637 | 0.075532 | 0.053396 | 0.109474 | 0.062614 | 0.044296 | 0.035432 |
| Ni Ref | 0.133042 | 0.063617 | 0.204683 | 0.034485 | 0.056616 | 0.139603 | 0.122887 | 0.116133 |
| Ti Ref | 0.278803 | 0.411628 | 0.284249 | 0.13885  | 0.137579 | 0.260656 | 0.051272 | 0.228277 |

|        | Ni1      | Ni2      | Ni3      | Ni4      | Ni5      | Ni6      | Ni7      | Ni8      |
|--------|----------|----------|----------|----------|----------|----------|----------|----------|
| Al Ref | 0.085835 | 0.129183 | 0.183033 | 0.062481 | 0.313211 | 0.124924 | 0.349926 | 0.151242 |
| Ni Ref | 0.072266 | 0.045385 | 0.05675  | 0.016411 | 0.133482 | 0.048103 | 0.190482 | 0.078671 |
| Ti Ref | 0.179993 | 0.407682 | 0.229391 | 0.252975 | 0.634033 | 0.240978 | 0.593748 | 0.359802 |

-continued

|  | Ni9 | Ni10 | Ni11 | Ni12 | Ni13 | Ni14 | Ni15 |
|---|---|---|---|---|---|---|---|
| Al Ref | 0.12815 | 0.140287 | 0.562584 | 0.389787 | 0.753441 | 0.716839 | 0.138661 |
| Ni Ref | 0.082583 | 0.077419 | 0.364564 | 0.204826 | 0.56232 | 0.527107 | 0.053419 |
| Ti Ref | 0.390094 | 0.229753 | 0.989806 | 0.741843 | 1.205438 | 1.162354 | 0.170464 |

|  | Ti1 | Ti2 | Ti3 | Ti4 | Ti5 | Ti6 | Ti7 | Ti8 |
|---|---|---|---|---|---|---|---|---|
| Al Ref | 0.01934 | 0.048615 | 0.111189 | 0.016643 | 0.039623 | 0.039914 | 0.147462 | 0.022902 |
| Ni Ref | 0.103921 | 0.248935 | 0.192621 | 0.147423 | 0.050824 | 0.038625 | 0.042339 | 0.068375 |
| Ti Ref | 0.049295 | 0.014819 | 0.036085 | 0.005862 | 0.078847 | 0.074154 | 0.172219 | 0.041347 |

|  | Ti9 | Ti10 | Ti11 | Ti12 | Ti13 | Ti14 | Ti15 | Ti16 |
|---|---|---|---|---|---|---|---|---|
| Al Ref | 0.016471 | 0.080716 | 0.019889 | 0.098569 | 0.029441 | 0.025438 | 0.011007 | 0.0203 |
| Ni Ref | 0.161337 | 0.273407 | 0.184478 | 0.204139 | 0.078159 | 0.062759 | 0.157186 | 0.0711 |
| Ti Ref | 0.00672 | 0.035022 | 0.005266 | 0.037342 | 0.045702 | 0.04902 | 0.013094 | 0.038996 |

For each case (small incident angle or grazing incident angle), a classifier is constructed. The classifier can be a binary (2-class) classifier or a 3-class classifier. The following Table C summarizes the classification accuracy for each combination.

TABLE C

Classification accuracy for each combination of metals

|  | Small incident angle | Grazing incident angle |
|---|---|---|
| Al—Ni | 67.74% | 90.32% |
| Al—Ti | 90.63% | 68.75% |
| Ni—Ti | 90.32% | 90.32% |
| Al—Ni—Ti | 72.34% | 72.34% |

It can be seen from Table C that for a binary classifier, good performance is obtained for Al—Ti and Ni—Ti with small incident angle, and good performance is obtained for Al—Ni and Ni—Ti with grazing incident angle.

Figure 1:
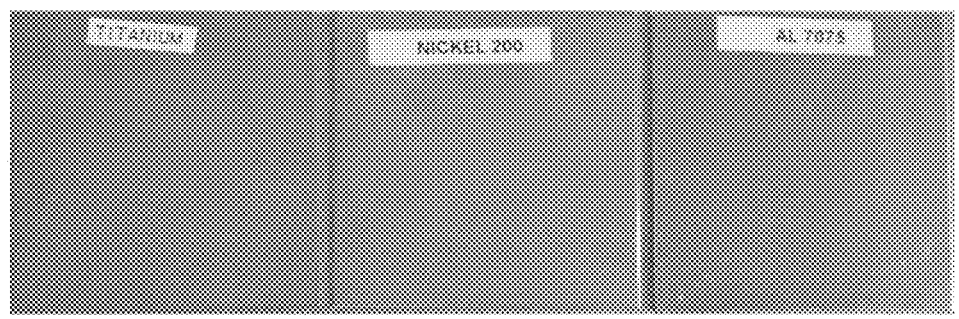
FIG. 1 shows an example of RGB images for samples of the metals titanium, nickel and aluminum, which appear quite similar to one another, and are thus difficult to classify using RGB images only.

In the embodiment described herein, as illustrated in FIGS. 1 through 3, the system is configured to take multiple shots (a minimum of two shots) that capture specular reflection at both small incident angle and grazing incident angle. In such an embodiment, the two features can be combined to construct a stronger 3-class classifier. For example, the distance $d_{small\ angle}$ for the small incident angle and the distance $d_{grazing\ angle}$ for the grazing incident angles can be combined into a combined distance $d_{combined}$ using weighting factors, such as the following in which each distance is weighted equally by a factor of one (1):

$$d_{combined}(x,X) = d_{small\ angle}(x,X) + d_{grazing\ angle}(x,X) \quad (5)$$

Of course, other ways of combining classifiers are possible. The following Table D shows the results using the above combined distance.

TABLE D

Classification accuracy for a combined distance metric $d_{combined}$.

|  | Al1 | Al2 | Al3 | Al4 | Al5 | Al6 | Al7 | Al8 |
|---|---|---|---|---|---|---|---|---|
| Al Ref | 0.091217 | 0.05668 | 0.048797 | 0.148887 | 0.068421 | 0.127988 | 0.059954 | 0.081181 |
| Ni Ref | 0.468754 | 0.171227 | 0.227252 | 0.179069 | 0.148247 | 0.187144 | 0.21031 | 0.148724 |
| Ti Ref | 0.323327 | 0.312855 | 0.226029 | 0.536499 | 0.45607 | 0.679877 | 0.612001 | 0.521168 |

|  | Al9 | Al10 | Al11 | Al12 | Al13 | Al14 | Al15 | Al16 |
|---|---|---|---|---|---|---|---|---|
| Al Ref | 0.132967 | 0.236241 | 0.254142 | 0.184038 | 0.1391 | 0.134012 | 0.109197 | 0.213403 |
| Ni Ref | 0.175707 | 0.126799 | 0.325543 | 0.119514 | 0.07768 | 0.178711 | 0.176363 | 0.241946 |
| Ti Ref | 0.400187 | 0.526316 | 0.347094 | 0.223027 | 0.342284 | 0.434188 | 0.15334 | 0.38091 |

|  | Ni1 | Ni2 | Ni3 | Ni4 | Ni5 | Ni6 | Ni7 | Ni8 |
|---|---|---|---|---|---|---|---|---|
| Al Ref | 0.12612 | 0.197687 | 0.238418 | 0.148004 | 0.47514 | 0.299123 | 0.524127 | 0.297 |
| Ni Ref | 0.102201 | 0.070652 | 0.074512 | 0.055742 | 0.22569 | 0.153018 | 0.30625 | 0.154678 |
| Ti Ref | 0.35202 | 0.573849 | 0.441294 | 0.77681 | 0.710192 | 0.38409 | 0.692437 | 0.509115 |

|  | Ni9 | Ni10 | Ni11 | Ni12 | Ni13 | Ni14 | Ni15 |
|---|---|---|---|---|---|---|---|
| Al Ref | 0.193598 | 0.212693 | 0.671134 | 0.507105 | 0.983622 | 0.957326 | 0.306056 |
| Ni Ref | 0.111872 | 0.10497 | 0.416537 | 0.264906 | 0.699419 | 0.681183 | 0.143019 |
| Ti Ref | 0.575122 | 0.399621 | 1.207737 | 0.863898 | 1.855837 | 1.881321 | 0.799143 |

|  | Ti1 | Ti2 | Ti3 | Ti4 | Ti5 | Ti6 | Ti7 | Ti8 |
|---|---|---|---|---|---|---|---|---|
| Al Ref | 0.212575 | 0.34357 | 0.31823 | 0.132674 | 0.307197 | 0.686953 | 0.474299 | 0.430221 |
| Ni Ref | 0.268976 | 0.497105 | 0.378195 | 0.249431 | 0.2835 | 0.607152 | 0.338089 | 0.428656 |
| Ti Ref | 0.063251 | 0.040295 | 0.051419 | 0.0571 | 0.086688 | 0.207997 | 0.1857 | 0.069589 |

TABLE D-continued

Classification accuracy for a combined distance metric $d_{combined}$.

| | Ti9 | Ti10 | Ti11 | Ti12 | Ti13 | Ti14 | Ti15 | Ti16 |
|---|---|---|---|---|---|---|---|---|
| Al Ref | 0.338582 | 0.242769 | 0.325884 | 0.284613 | 0.276714 | 0.114881 | 0.112267 | 0.128326 |
| Ni Ref | 0.444918 | 0.415727 | 0.455506 | 0.372017 | 0.292596 | 0.135448 | 0.252187 | 0.160165 |
| Ti Ref | 0.046309 | 0.059034 | 0.018507 | 0.052683 | 0.066838 | 0.13192 | 0.069028 | 0.09622 |

The classification accuracy of the resulting 3-class classifier is 93.62%.

Other Embodiments

According to other embodiments contemplated by the present disclosure, example embodiments may include a computer processor such as a single core or multi-core central processing unit (CPU) or micro-processing unit (MPU), which is constructed to realize the functionality described above. The computer processor might be incorporated in a stand-alone apparatus or in a multi-component apparatus, or might comprise multiple computer processors which are constructed to work together to realize such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. For these purposes, access to the non-transitory computer-readable storage medium may be a local access such as by access via a local memory bus structure, or may be a remote access such as by access via a wired or wireless network or Internet. The computer processor(s) may thereafter be operated to execute the computer-executable program or program steps to perform functions of the above-described embodiments.

According to still further embodiments contemplated by the present disclosure, example embodiments may include methods in which the functionality described above is performed by a computer processor such as a single core or multi-core central processing unit (CPU) or micro-processing unit (MPU). As explained above, the computer processor might be incorporated in a stand-alone apparatus or in a multi-component apparatus, or might comprise multiple computer processors which work together to perform such functionality. The computer processor or processors execute a computer-executable program (sometimes referred to as computer-executable instructions or computer-executable code) to perform some or all of the above-described functions. The computer-executable program may be pre-stored in the computer processor(s), or the computer processor(s) may be functionally connected for access to a non-transitory computer-readable storage medium on which the computer-executable program or program steps are stored. Access to the non-transitory computer-readable storage medium may form part of the method of the embodiment. For these purposes, access to the non-transitory computer-readable storage medium may be a local access such as by access via a local memory bus structure, or may be a remote access such as by access via a wired or wireless network or Internet. The computer processor(s) is/are thereafter operated to execute the computer-executable program or program steps to perform functions of the above-described embodiments.

The non-transitory computer-readable storage medium on which a computer-executable program or program steps are stored may be any of a wide variety of tangible storage devices which are constructed to retrievably store data, including, for example, any of a flexible disk (floppy disk), a hard disk, an optical disk, a magneto-optical disk, a compact disc (CD), a digital versatile disc (DVD), micro-drive, a read only memory (ROM), random access memory (RAM), erasable programmable read only memory (EPROM), electrically erasable programmable read only memory (EEPROM), dynamic random access memory (DRAM), video RAM (VRAM), a magnetic tape or card, optical card, nanosystem, molecular memory integrated circuit, redundant array of independent disks (RAID), a nonvolatile memory card, a flash memory device, a storage of distributed computing systems and the like. The storage medium may be a function expansion unit removably inserted in and/or remotely accessed by the apparatus or system for use with the computer processor(s).

This disclosure has been presented for purposes of illustration and description but is not intended to be exhaustive or limiting. Many modifications and variations will be apparent to those of ordinary skill in the art who read and understand this disclosure, and this disclosure is intended to cover any and all adaptations or variations of various embodiments. The example embodiments were chosen and described in order to explain principles and practical application, and to enable others of ordinary skill in the art to understand the nature of the various embodiments. Various modifications as are suited to particular uses are contemplated. Suitable embodiments include all modifications and equivalents of the subject matter described herein, as well as any combination of features or elements of the above-described embodiments, unless otherwise indicated herein or otherwise contraindicated by context or technological compatibility or feasibility.

The invention claimed is:

1. A method for material classification of a specular sample fabricated from an unknown material, the method comprising:
   obtaining a measurement of a specular reflection of the sample at at least one observation angle and in at least two spectral bands including a first spectral band and a second spectral band;
   calculating a feature vector using a homogeneous function that combines the measured specular reflections in the first and second spectral bands; and
   classifying the sample based on the feature vector;
   wherein the homogeneous function includes a ratio of values of the first and second spectral bands of the measured specular reflections, and
   wherein the feature vector is based on a histogram of ratio values of the first and second spectral bands of the measured specular reflections.

2. The method of claim 1, wherein the specular sample is a metallic sample fabricated from an unknown metal.

3. The method of claim 1, further comprising positioning of the sample relative to an illumination source and the observation angle so as to generate the specular reflection from the sample.

4. The method of claim 1, wherein the histogram of ratio values is based on ratio values from a selected region of pixels of the captured image that corresponds to a specular highlight.

5. The method of claim 4, wherein the selected region is defined by a mask derived from the captured image of the specular reflection.

6. The method of claim 1, wherein classifying includes determining a distance between the histogram of the sample and a histogram of a reference sample in a predetermined database.

7. The method of claim 6, wherein multiple histograms are associated with a reference sample in the predetermined database, and a distance between the sample and the reference sample is taken to be a minimum of distances of the histogram of the sample from the multiple histograms of the reference sample.

8. The method of claim 7, wherein multiple measurements are taken at a respective multiplicity of observation angles including a grazing incident angle and a small incident angle.

9. The method of claim 8, wherein a histogram of ratio values of the first and second spectral bands of the measured specular reflections is obtained for each observation angle, resulting in multiple histograms of ratio values each respectively corresponding to one of the multiple observation angles, and classification is based on a distance between the multiple histograms of the sample and the multiple histograms of a reference sample in the predetermined database.

10. The method of claim 9, wherein the histograms are weighted by weighting factors that depend on specific materials being differentiated.

11. The method of claim 1, wherein classifying includes determining a distance between the feature vector of the sample and a feature vector of a reference sample in a predetermined database of labeled samples.

12. The method of claim 11, wherein multiple feature vectors are associated with a reference sample in the predetermined database, and a distance between the sample and the reference sample is taken to be a minimum of distances of the feature vector of the sample from the multiple feature vectors of the reference sample.

13. The method of claim 12, wherein multiple measurements are taken at a respective multiplicity of observation angles including a grazing incident angle and a small incident angle.

14. The method of claim 13, wherein a feature vector is obtained for each observation angle, resulting in multiple feature vectors each respectively corresponding to one of the multiple observation angles, and classification is based on a distance between the multiple feature vectors of the sample and the multiple feature vectors of a reference sample in the predetermined database.

15. The method of claim 14, wherein the feature vectors are weighted by weighting factors that depend on specific materials being differentiated.

16. An apparatus for material classification of a specular sample fabricated from an unknown material, comprising:

memory for storing computer-executable process steps; and one or more processors for executing the computer-executable process step stored in the memory;

wherein the computer-executable process steps include steps to:

obtain a measurement of a specular reflection of the sample at at least one observation angle and in at least two spectral bands including a first spectral band and a second spectral band;

calculate a feature vector using a homogeneous function that combines the measured specular reflections in the first and second spectral bands; and classify the sample based on the feature vector;

wherein the homogeneous function includes a ratio of values of the first and second spectral bands of the measured specular reflections, and wherein the feature vector is based on a histogram of ratio values of the first and second spectral bands of the measured specular reflections.

17. A non-transitory computer-readable storage medium which stores computer-executable process steps for material classification of a specular sample fabricated from an unknown material, which when executed by a computer causes the computer to perform steps including:

obtaining a measurement of a specular reflection of the sample at at least one observation angle and in at least two spectral bands including a first spectral band and a second spectral band;

calculating a feature vector using a homogeneous function that combines the measured specular reflections in the first and second spectral bands; and classifying the sample based on the feature vector;

wherein the homogeneous function includes a ratio of values of the first and second spectral bands of the measured specular reflections, and wherein the feature vector is based on a histogram of ratio values of the first and second spectral bands of the measured specular reflections.

* * * * *